(12) United States Patent
Nomura et al.

(10) Patent No.: US 8,338,647 B2
(45) Date of Patent: Dec. 25, 2012

(54) METHOD FOR PRODUCING TERTIARY AMINE

(75) Inventors: Wataru Nomura, Wakayama (JP); Shoji Hasegawa, Wakayama (JP)

(73) Assignee: Kao Corporation, Tokyo (JP)

( * ) Notice: Subject to any disclaimer, the term of this patent is extended or adjusted under 35 U.S.C. 154(b) by 268 days.

(21) Appl. No.: 12/678,226

(22) PCT Filed: Sep. 18, 2008

(86) PCT No.: PCT/JP2008/067366
§ 371 (c)(1),
(2), (4) Date: May 3, 2010

(87) PCT Pub. No.: WO2009/038223
PCT Pub. Date: Mar. 26, 2009

(65) Prior Publication Data
US 2010/0217044 A1 Aug. 26, 2010

(30) Foreign Application Priority Data
Sep. 20, 2007 (JP) .................................. 2007-243489

(51) Int. Cl.
*C07C 209/16* (2006.01)
(52) U.S. Cl. ........................................ 564/479; 564/480
(58) Field of Classification Search .................. None
See application file for complete search history.

(56) References Cited

U.S. PATENT DOCUMENTS

| 5,925,793 | A | 7/1999 | Mueller |
| 2005/0283025 | A1* | 12/2005 | Hirota et al. .................. 564/478 |
| 2007/0179320 | A1* | 8/2007 | Hirota et al. .................. 564/478 |
| 2008/0004472 | A1 | 1/2008 | Nishimura et al. |
| 2010/0305363 | A1 | 12/2010 | Hirota et al. |

FOREIGN PATENT DOCUMENTS

| CN | 1876224 A | 12/2006 |
| JP | 6-211754 A | 8/1994 |
| JP | 2006-102709 A | 4/2006 |
| WO | WO 2005/035122 A1 | 4/2005 |

OTHER PUBLICATIONS

Chinese Office Action for Chinese Application No. 200880107697.5 dated Aug. 17, 2012 with English translation.

* cited by examiner

*Primary Examiner* — Brian J Davis
(74) *Attorney, Agent, or Firm* — Birch, Stewart, Kolasch & Birch, LLP

(57) ABSTRACT

The present invention provides a method for producing a tertiary amine by reacting an alcohol with a primary or secondary amine in the presence of a film catalyst containing a thermosetting resin and an active metal, wherein the film catalyst is reduced at 100 to 150° C., and a method for activating the film catalyst containing a thermosetting resin and an active metal, including applying a coating agent containing the thermosetting resin and a powder catalyst onto the surface of a support, drying the resultant, curing it at 80 to 170° C., and reducing the catalyst at 100 to 150° C.

8 Claims, 2 Drawing Sheets

METHOD FOR PRODUCING TERTIARY AMINE

FIELD OF THE INVENTION

The present invention relates to a method for producing a tertiary amine in the presence of a film catalyst and a method for activating the film catalyst.

BACKGROUND OF THE INVENTION

Many industrial reactions use a mixing tank reactor with slurry of a solid catalyst. In the reactor, liquid is contacted with a reactive gas such as hydrogen or ammonia gas in the presence of the catalyst to progress a reaction. After the reaction, the catalyst is generally removed by filtration, and a reaction product is collected.

However, the catalyst in a slurry form has problems in safety, increased amount of waste, operability, productivity, and the like. For example, many of catalysts are pyrophoric, and catalysts in forms of powder and slurry require careful handling. These catalysts also have problems of complicated facilities and operations, because these must be removed by, for example, filtration to collect a reaction product.

One of processes that do not require operations for mixing such as stirring and bubbling with gas and for separating a catalyst by filtration is a fixed-bed process. For a formed catalyst used in the fixed-bed process, those have conventionally been known, including pellet, noodle, and tablet catalysts. A powder material having a catalytic activity is molded, for example by pressing or extruding, into an intended structure being very porous and having both the above shown form and a large surface area. For example, JP-A 6-211754 discloses such a catalyst.

The fixed-bed process can solve problems such as handling of a catalyst and waste, but is applicable to not so much reactions. For example, in endothermic and exothermic reactions, there are problems of temperature control, nonuniform distribution of liquid-gas in a reactor to result in insufficient reaction rate, and topically concentrated distribution to cause side reactions.

A reaction of an alcohol with a primary or secondary amine in the presence of a formed catalyst described in JP-A 6-211754 in order to produce a tertiary amine at high reaction rate results in not a little amount of undesired bi-products. Examples of the bi-product include waxes and aldol condensation products from the starting alcohol by side reactions, ammonias derived from disproportionation of the primary or secondary amine, and tertiary amines produced by side reactions of the primary or secondary amine. To highly selectively produce an intended product with a reduced amount of such bi-products, many attempts to improve the method have been done. However, the reaction has been difficult to be performed at high selectivity by a simple process in the past.

To overcome the disadvantage of production of a tertiary amine in the presence of such a formed catalyst, WO-A2005/035122 discloses a method of producing a tertiary amine in the presence of a film catalyst.

SUMMARY OF THE INVENTION

The present invention provides a method for producing a tertiary amine, including reacting an alcohol with a primary or secondary amine in the presence of a film catalyst containing a thermosetting resin and an active metal, wherein the film catalyst is reduced at 100 to 150° C.

The present invention also provides a method for activating a film catalyst containing a thermosetting resin and an active metal, including applying a coating agent containing the thermosetting resin and a powder catalyst onto a surface of a support, drying the resultant, curing it at 80 to 170° C., and reducing the catalyst at 100 to 150° C.

The present invention also provides use of a film catalyst containing a thermosetting resin and an active metal and being reduced at 100 to 150° C. for production of a tertiary amine by reacting an alcohol with a primary or secondary amine.

The present invention also provides use of a film catalyst containing a thermosetting resin and an active metal and being produced by applying a coating containing the thermosetting resin and a powder catalyst onto a surface of a support, drying the resultant, curing it at 80 to 170° C., and reducing the catalyst at 100 to 150° C. for production of a tertiary amine by reacting an alcohol with a primary or secondary amine.

Figure 1:
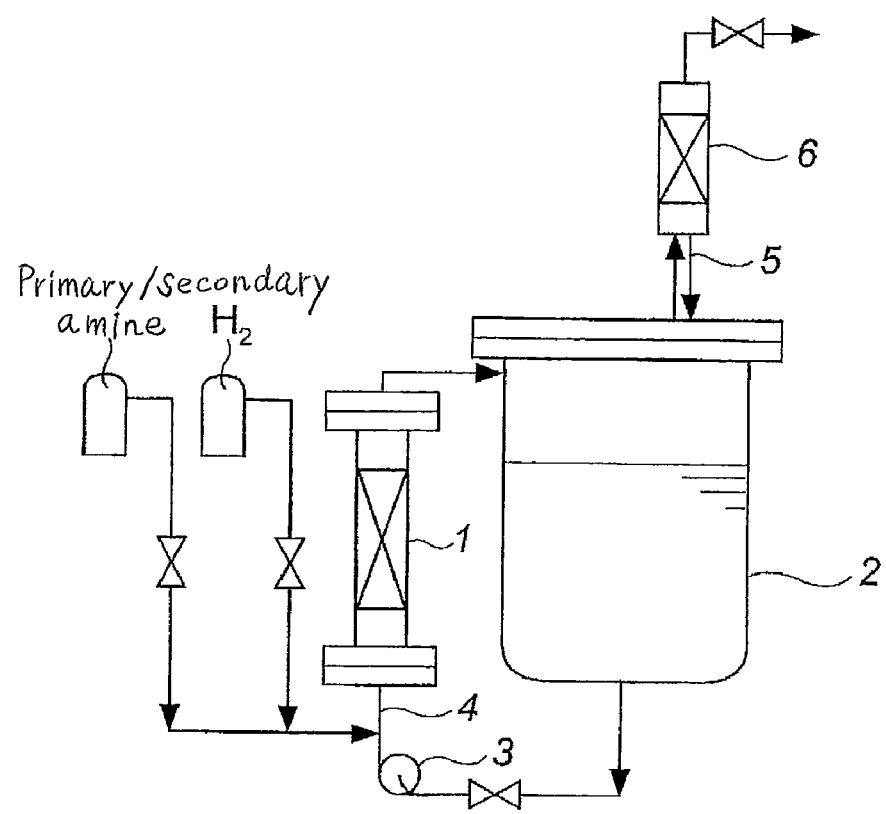
FIG. 1 shows a schematic diagram of an example of a circulating fixed-bed reactor used in the present invention.

Numbers in Figures show the followings:
1 Tube reactor loaded with film catalyst
2 Buffer tank
3 External circulation pump
4 External circulation conduit
5 Conduit for packed tower
6 Packed tower
7 Reaction tank
8 Film catalyst
9 Filter plate
10 Conduit
11 Conduit
12 Condenser

DETAILED DESCRIPTION OF THE INVENTION

There is still demand for a method for producing an intended tertiary amine at higher selectivity and higher yield than conventional methods.

The present invention provides a method for producing a tertiary amine from an alcohol and a primary or secondary amine at high yield and efficiency.

According to the method of the present invention, an intended tertiary amine can be produced at high yield and efficiency with a simple process without an operation for separating a catalyst.

Examples of the starting alcohol used in the method for producing a tertiary amine of the present invention include linear and branched, saturated and unsaturated aliphatic alcohols having 8 to 36 carbon atoms. Specific examples include octyl alcohol, lauryl alcohol, myristyl alcohol, stearyl alcohol, behenyl alcohol, oleyl alcohol, mixed alcohols thereof, Ziegler alcohols produced by the Ziegler method, oxo alcohols produced by the oxo method, and Guerbet alcohols.

Examples of the starting primary or secondary amine used in the method for producing a tertiary amine of the present invention include aliphatic primary and secondary amines such as methylamine, dimethylamine, ethylamine, diethylamine, dodecylamine, and didodecylamine.

A corresponding tertiary amine is produced from these starting alcohol and primary or secondary amine through substitution of a hydrogen atom connecting to a nitrogen atom of the primary or secondary amine with an alkyl and/or alkenyl group derived from the alcohol. For example, a corresponding tertiary amine produced from lauryl alcohol and dimethylamine is N-dodecyl-N,N-dimethylamine. This should be distinguished from tertiary amine byproducts, N,N-didodecyl-N-methylamine and N,N,N-tridodecylamine, formed by reaction between methylamine, generated by disproportionation of dimethylamine, and ammonia.

The film catalyst used in the present invention is in the form of film having a thickness of not more than 500 μm, unlike a conventional catalyst in the form of nonuniform filler having a size of few mm. Migration of a reactant and a product in a catalyst body is under diffusion control. A short migration distance of not more than 500 facilitates transport of substances into and out of the catalyst body, thereby making effective use of the inside of the catalyst body and controlling an overreaction of an intermediate in the catalyst body. A thickness of the film catalyst is particularly preferably not more than 100 μm, and more preferably not more than 50 μm, because reaction activity per mass of the catalyst is significantly increased. From the viewpoints of ensuring strength of a catalyst layer and durability in strength, the lower limit of the thickness is 0.01 and more preferably 1 μm.

A structure of the film catalyst can be of any style according to a reactor form. Examples of the structure include a catalyst-coated layer formed on the inner surface of a tube and a thin plate catalyst partitioning a tube into flow passages in the axial direction. These structures are suitably used in a flow-through type tubular reactor. The structure may also be a catalyst-coated layer formed on the surface of a fin plate of an open style installed in a tank. This structure is suitably used in a tank reactor. In any case, the film catalyst has a preferable structure so that reactants may be easily supplied to the catalyst and reaction products may be easily collected from the catalyst. The surface area of the catalyst on which the supply of reactants and the collection of reaction products occur may be made as large as possible for effective reaction progresses. To satisfy the requirement, preferred are structures such as a bundle of tubes having an inner diameter of few mm to several tens of mm or a honey-comb structure having a cell density of several tens to several hundreds cell per square inch, having a film catalyst on an inner wall thereof.

One of methods of forming a film catalyst having the structure described above is forming a substance having catalytic activities into a honeycomb structure, for example. From the viewpoint of achieving both a thin catalyst layer and high mechanical strength, a film catalyst is preferably fixed on the surface of a support, and more preferably of a metal foil support. For example, the surface of a support of metal or material having rigidity in the form of tube, plane, or honeycomb is coated with a coating agent containing a substance having catalytic activity to form a layer as a film catalyst. At this time, coating can be performed by known methods, including a blade coating using a binder, spraying, dipping, spin coating, gravure coating, and die coating.

The active metal composing the film catalyst used in the present invention is not specifically limited as long as it has catalytic activities. Any known metal can be used. Preferably used are generally copper series metals, and more preferably those containing copper. Examples thereof include Cu single metal and binary metals of Cu with transition metal elements such as Cr, Co, Ni, Fe, Mn, and Zn. Preferably used is a binary metal of Cu and Ni. Ternary or more metals further containing platinum group elements such as Pt, Pd, and Ru may also be preferably used. These metals may be used in the state of being supported on a carrier such as silica, alumina, titania, and zeolite.

The film catalyst used in the present invention contains the thermosetting resin that does not act as an active substance by itself but serves as a binder for fixing an active substance to form a catalyst body in the form of film. For the thermosetting resin, preferably used are those having properties of binding the active substance to the active substance or the surface of the support, resisting against reaction environments, having no adverse effect on a reaction system, and being chemical resistant and heat resistant. Examples of the thermosetting resin include phenol resins, furan resins, and epoxy resins. Preferred are phenol resins.

The film catalyst used in the present invention may further contain other binder than the thermosetting resin, including thermoplastic resins and inorganic compound sol such as silica and alumina.

An internal structure of the film catalyst used in the present invention, which largely depends on a kind of the active substance composing the catalyst body and a method of producing the catalyst body, can be porous when formed on the surface of a support by a wet or dry method of applying with the active substance in the form of powder.

Examples of the method for producing the film catalyst used in the present invention include forming a film on a support with a coating agent containing a powder catalyst and a thermosetting resin as a binder for fixing the powder catalyst.

The powder catalyst used in the method of forming a film can be prepared using a catalyst carrier and a precursor of a catalytically active substance. Examples of the catalyst carrier include activated charcoal, alumina, silica, zeolite, titania, silica-alumina, and diatomaceous earth. Examples of the precursor of a catalytically active substance include sulfates, nitrates, ammonium complexes, acetates, oxalates, acetyl acetonates, and chlorides of transition metal elements such as Cu, Ni, Zn, Co, Fe, Cr, and Mn and platinum group elements such as Pt, Pd, and Ru. The powder catalyst can be prepared using these catalyst carriers and precursors of a catalytically active substance by general known methods such as impregnation, co-impregnation, co-precipitation, and ion-exchange.

In the method of forming a film, first, to the powder catalyst are added the thermosetting resin and a solvent and pre-mixed to give a pre-mixture. Pre-mixing may be conducted for 5 to 60 minutes with Disper or the like. In pre-mixing, from the viewpoints of achieving good catalytic activity and preventing a dropped coated film, a mixing ratio of the thermosetting resin to the powder catalyst is preferably 20 to 80 parts by mass, more preferably 30 to 70 parts by mass, and even more preferably 40 to 60 parts by mass of the thermosetting resin to 100 parts by mass of the powder catalyst. Also in pre-mixing, from the viewpoints of dispersibility and efficiency of a coating agent, a solid content is preferably 10 to 80% by mass, more preferably 20 to 70% by mass, and even more preferably 25 to 65% by mass. Examples of the solvent used in pre-mixing include ketone solvents such as methylethylketone, methylisobutylketone, and acetone.

Next, the pre-mixture is mixed and dispersed to give a coating agent. Mixing and dispersing can be performed with, for example, a paint shaker, a basket mill, a grain mill, a Dino mill, and an agitating mill. A time of mixing and dispersing is preferably 30 to 120 minutes.

Specific examples of the method of forming a film of a coating agent on a support include applying the coating agent containing the powder catalyst and the thermosetting resin on the surface of the support by blade coating, roll coating, knife coating, bar coating, spraying, dipping, spin coating, comma coating, kiss coating, gravure coating, dye coating, and the like. Preferred is a method of applying on a metal foil face of the support such as copper foil with a gravure coater.

An applied coating agent is preferably dried and cured. The drying and curing treatment is preferably performed by placing the coating agent in a heated atmosphere such as of the air, vapor, or inert gas (e.g., nitrogen, and argon) or blowing such a heat medium to the coating agent. The treatment can also be performed by various methods such as a method using heat of infrared and/or far-infrared radiation and a method of heating with an induced current by an electromagnetic wave. The treatment can also be performed by a combination of these methods or a method of drying in the air at ambient temperature (air-drying).

Preferred conditions of drying are, for example, a temperature of 80 to 150° C. and a time of 30 seconds. A dried product may be further formed by cutting or bending according to need. From the viewpoint of efficiency of curing, a temperature at the curing treatment is preferably not lower than 80° C. From the viewpoint of production of a tertiary amine at high activity, the temperature is preferably not higher than 170° C. Putting together, the temperature is preferably 80 to 170° C., and more preferably 90 to 150° C. A time for the curing treatment is preferably 30 to 300 minutes, and more preferably 60 to 150 minutes.

In the method for producing a tertiary amine of the present invention, the film catalyst reduced at 100 to 150° C. is used. It means that the method includes a step of reducing the catalyst before reacting the alcohol with the amine. Reduction of the catalyst is preferably performed by supplying a hydrogen gas to the reactor loaded with the cured film catalyst, and more preferably in the presence of the starting alcohol. Specific examples of the method of reduction include a method of supplying a hydrogen gas and the starting alcohol to a reactor loaded with the cured film catalyst to reduce the catalyst and a method of supplying a hydrogen gas to the reactor loaded with the cured film catalyst and the starting alcohol to reduce the catalyst. A hydrogen gas is preferably supplied at a gas space velocity of 1 to 1000 (1/hr), more preferably 10 to 500 (1/hr), and even more preferably 20 to 300 (1/hr).

From the viewpoint of efficacy of reduction, a temperature at the reduction step is not lower than 100° C. From the viewpoint of production of a tertiary amine at high activity, the temperature is preferably not higher than 150° C. That is, the reduction temperature is 100 to 150° C., preferably 110 to 140° C. A time for reduction is preferably 30 to 600 minutes, and more preferably 60 to 500 minutes.

Any type of a reactor including various known reactors can be used for the reactor loaded with the film catalyst in the present invention. For example, a tube reactor may be loaded with the film catalyst rolled to a cylindrical shape or cut into a strip. A shell-and-tube heat exchanger type reactor may also be used by loading with the film catalyst in a tube or shell part. In this case, a heating medium flows to the tube or shell not loaded with the film catalyst to control a temperature of a reaction part. In cases of a circulation type tubular reactor, the reaction can be progressed continuously by feeding a reactant to the film catalyst in the tube and collecting a production mixture from the reactor in a circulatory manner.

FIG. 1 shows an example of the reactor used in the method for producing a tertiary amine of the present invention, which is a circulating fixed-bed reactor. Reference numeral 1 denotes a tube reactor loaded with a film catalyst, reference numeral 2 denotes a buffer tank, reference numeral 3 denotes an external circulation pump, reference numeral 4 denotes an external circulation conduit, reference numeral 5 denotes a conduit for packed tower, and reference numeral 6 denotes a packed tower.

The tube reactor 1 is an upright cylindrical fixed-bed reactor loaded with the film catalyst therein. A temperature of the reactor is controlled by external heating. The buffer tank 2 is for storing a reactant and/or mixture thereof with a product in the liquid state. The pump 3 circulates the reactant and/or the mixture thereof between the reactor 1 and the buffer tank 2. Through the conduit 4, from the bottom of the reactor 1, the reactant and/or the mixture thereof with the product, a gaseous primary or secondary amine, and a hydrogen gas are continuously supplied thereto, and from the top of the reactor 1, an unreacted reactant and/or mixture thereof with the product and a hydrogen gas are continuously collected and sent into the buffer tank 2. An unreacted gaseous primary or secondary amine and water are continuously drained off through the conduit 5. A mixture drained through the conduit 5 contains ingredients described above and sometimes the alcohol and/or the produced tertiary amine in the form of vapor or mist. The packed tower 6 condenses such vapor or mist to the liquid state and returns it to the buffer tank 2. Other gaseous ingredients are removed off from the reaction system. The reaction system is kept to about normal pressure.

A reactant liquid may be supplied to the reactor 1 as an upward flow shown in FIG. 1 or a downward flow. The reactor is preferably under controlled temperature with general means including a jacket and a pipe for heat exchange arranged in the reactor.

Figure 2:
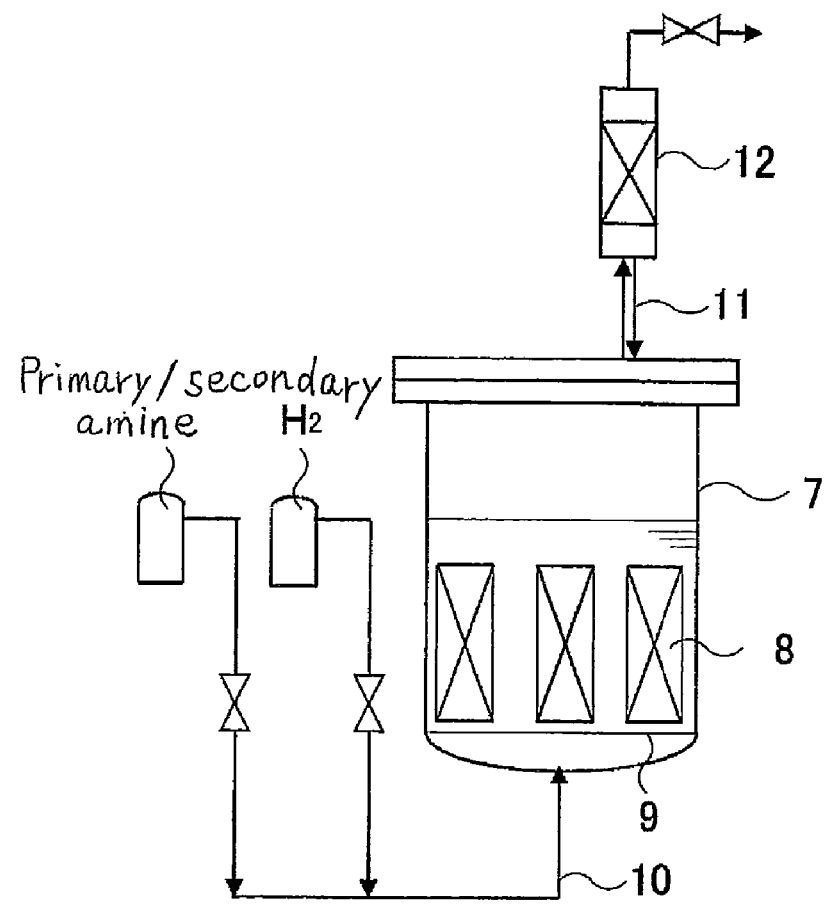
FIG. 2 shows a schematic diagram of an example of a bubbling tank reactor used in the present invention.

FIG. 2 shows another example of the reactor used in the method for producing a tertiary amine of the present invention, which is a bubbling tank reactor. In FIG. 2, reference numeral 7 denotes a reaction tank, reference numeral 8 denotes a film catalyst, reference numeral 9 denotes a filtering plate, reference numerals 10 and 11 denote conduits, and reference numeral 12 denotes a condenser.

The reaction tank 7 is loaded with the film catalyst 8. The reaction tank 7 contains a reactant and/or mixture thereof with a product in the liquid state. A temperature of the liquid is controlled by external heating. A gaseous primary or secondary amine and a hydrogen gas flow through the conduit 10 and pass through the filtering plate 9 installed at the bottom of the reaction tank 7 to be continuously supplied to and reacted in the reaction tank 7. Through the conduit 11, an unreacted gaseous primary or secondary amine and water are continuously drained off. A mixture drained through the conduit 11 contains ingredients described above and sometimes the alcohol and/or the produced tertiary amine in the form of vapor or mist. The condenser 12 condenses such vapor or mist to the liquid state and returns it to the reaction tank 7. Other gaseous ingredients are removed off from the reaction system. The reaction system is kept to about normal pressure.

In the method for producing a tertiary amine of the present invention, conditions of the reaction between the alcohol and the primary or secondary amine are varied according to kinds of a reactant, a product, and a catalyst. The reactant may be in a gas phase or a liquid phase. When the reaction system contains a gas phase, the reaction is preferably conducted under an atmosphere of hydrogen, nitrogen and/or rare gas for keeping activity of the catalyst. When the reaction system contains gas and liquid phases and the alcohol and the primary or secondary amine are present in different phases, transport of substances between phases is preferably facilitated by bubbling the gas in the liquid or the like. It is also possible to facilitate transport of substances between phases by supplying a reactant in a gas-liquid mixed phase to a reactive site in which narrow flow passages having a diameter of few mm or smaller are formed with the film catalyst.

An alcohol used in the reduction may be used as it is in the reaction after the reduction, or wholly substituted with new alcohol that is used as the starting alcohol for the reaction. A kind of the alcohol used in the reaction may be the same as or different from that of the alcohol used in the reduction.

A pressure in the reaction system is preferably not so large over an ambient pressure. A reaction temperature, which may be varied according to a kind of the catalyst, is preferably at 150 to 300° C. Water generated as a bi-product during the reaction is drained off from the reaction system to facilitate progress of the reaction and keep activity of the catalyst.

According to the present invention, a tertiary amine can be produced at high yield and efficiency.

EXAMPLES

The following Examples demonstrate the present invention. Examples are intended to illustrate the present invention and not to limit the present invention.

In Examples, "%" and "parts" refer to "% by mass" and "parts by mass", respectively, unless otherwise specified.

In reduction in Examples 1 to 3 and Comparative Example 1, reduced film catalysts were analyzed by X-ray diffraction to confirm that 95% or more CuO in each catalyst was reduced to Cu metal.

Preparation Example of Powder Catalyst

In a 1 L tank, a synthetic zeolite and an aqueous solution of copper nitrate, nickel nitrate, and ruthenium chloride at a molar ratio of metal atoms of Cu:Ni:Ru=4:1:0.01 were stirred and heated to 90° C. At the temperature, a 10% aqueous solution of sodium carbonate was gradually added dropwise at a controlled pH of 9 to 10. The mixture was aged for 1 hour. A precipitate was filtered, washed with water, dried for 10 hours at 80° C., and baked for 3 hours at 600° C. to give a powder catalyst. The resultant powder catalyst (hereinafter, referred to as powder catalyst a) contained 50% of metal oxide and 50% of synthetic zeolite.

Production Example 1

In a 250 ml wide-mouth polyethylene bottle, methylisobutylketone (MIBK) as a solvent, phenol resin (PR-9480, manufactured by Sumitomo Bakelite Co., Ltd.) as a binder, and the above prepared powder catalyst a were placed in this order. A mixing ratio was 20 parts of nonvolatile matters of the phenol resin to 80 parts (65 g) of the powder catalyst a. An amount of MIBK was such that a solid content of a mixture was 60%. Glass beads having a diameter of 1 mm (apparent volume: 65 ml) as a dispersing medium were further added to the wide-mouth polyethylene bottle. The wide-mouth polyethylene bottle was set in a paint shaker and subjected to a shaking and dispersing treatment for 30 minutes as a preparation time to give a coating agent.

On both sides of copper foil (thickness: 40 µm, a sheet of 6.5 cm by 410 cm), which was used as a support, the coating agent was applied with a bar coater and dried for 30 seconds at 150° C. A half of the dried product was corrugated and folded on the other half of a flat plate. The layered product was rolled up and cured for 90 minutes at 150° C. to give a film catalyst A having the catalyst a fixed on both sides of the copper foil. For the resultant film catalyst A, a thickness of one side excluding the copper foil, a mass of the catalyst excluding the copper foil, and a surface area of the film catalyst were as shown in Table 1.

Production Example 2

In a 250 ml wide-mouth polyethylene bottle, MIBK as a solvent, phenol resin (PR-9480, manufactured by Sumitomo Bakelite Co., Ltd.) as a binder, and the powder catalyst a prepared above were placed in this order. A mixing ratio was 25 parts of nonvolatile matters of the phenol resin to 75 parts (65 g) of the powder catalyst a. An amount of MIBK was such that a solid content of a mixture was 60%. Glass beads having a diameter of 1 mm (apparent volume: 65 ml) as a dispersing medium were further added to the wide-mouth polyethylene bottle. The wide-mouth polyethylene bottle was set in a paint shaker and subjected to a shaking and dispersing treatment for 30 minutes as a preparation time to give a coating agent.

On both sides of copper foil (thickness: 40 µm, a sheet of 6.5 cm by 410 cm), which was used as a support, the coating agent was applied with a bar coater and dried for 30 seconds at 150° C. A half of the dried product was corrugated and layered on the other half. The layered product was rolled up and cured for 90 minutes at 150° C. to give a film catalyst B having the catalyst a fixed on both sides of the copper foil. For the resultant film catalyst B, a thickness of one side excluding the copper foil, a mass of the catalyst excluding the copper foil, and a surface area of the film catalyst were as shown in Table 1.

Production Example 3

In a 250 ml wide-mouth polyethylene bottle, MIBK as a solvent, phenol resin (PR-9480, manufactured by Sumitomo Bakelite Co., Ltd.) as a binder, and the powder catalyst a prepared above were placed in this order. A mixing ratio was 25 parts of nonvolatile matters of the phenol resin to 75 parts (65 g) of the powder catalyst a. An amount of MIBK was such that a solid content of a mixture was 60%. Glass beads having a diameter of 1 mm (apparent volume: 65 ml) as a dispersing medium were further added to the wide-mouth polyethylene bottle. The wide-mouth polyethylene bottle was set in a paint shaker and subjected to a shaking and dispersing treatment for 30 minutes as a preparation time to give a coating agent.

On both sides of copper foil (thickness: 40 µm, a sheet of 6.5 cm by 410 cm), which was used as a support, the coating agent was applied with a bar coater and dried for 30 seconds at 150° C. A half of the dried product was corrugated and folded on the other half of a flat plate. The layered product was rolled up and cured for 90 minutes at 100° C. to give a film catalyst C having the catalyst a fixed on both sides of the copper foil. For the resultant film catalyst C, a thickness of one side excluding the copper foil, a mass of the catalyst excluding the copper foil, and a surface area of the film catalyst were as shown in Table 1.

TABLE 1

|  |  | Production example 1 | Production example 2 | Production example 3 |
|---|---|---|---|---|
| Name of film catalyst |  | Catalyst A | Catalyst B | Catalyst C |
| Curing temperature | [° C.] | 150 | 150 | 100 |
| Curing time | [minutes] | 90 | 90 | 90 |
| Thickness[*1] | [µm] | 10 | 50 | 50 |
| Amount of catalyst[*2] | [g-film catalyst] | 3.2 | 26 | 26 |
| Surface area of film catalyst | [m$^2$] | 0.2 | 0.55 | 0.55 |

[*1] Thickness of a side of the catalyst layer excluding copper foil
[*2] Mass of the film catalyst mass excluding copper foil Example 1

Using a circulating fixed-bed reactor shown in FIG. 1, N-dodecyl-N,N-dimethylamine was produced from lauryl alcohol and dimethylamine by the method described below.

The film catalyst A, prepared in Production Example 1, was put in the tube reactor 1 having an inner diameter of 28.4 mm. A volume of a part loaded with the film catalyst A was 0.08 L and a plurality of flow paths each having a sectional area of about 0.1 cm², running in the axial direction of the reactor 1, were formed from the film-type catalyst A. 750 g of lauryl alcohol (Kalcol 20, manufactured by Kao Corporation) was charged in the buffer tank 2. While supplying a hydrogen gas to the tube reactor 1 at 16.5 L/hr based on a standard state volume, or a gas space velocity of 206 (1/hr), a reaction mixture was circulated at 5.9 L/hr between the buffer tank 2 and the tube reactor 1. 6 hours after an inside temperature of the tube reactor 1 reached 130° C., reduction of the catalyst was stopped, and the whole mixtures in the buffer tank 2 and the tube reactor 1 were drained.

After the reduction of the catalyst, 750 g of lauryl alcohol (Kalcol 20, manufactured by Kao Corporation) was charged in the buffer tank 2. While supplying a hydrogen gas to the tube reactor 1 at 16.5 L/hr based on a standard state volume, a reaction mixture was circulated at 5.9 L/hr between the buffer tank 2 and the tube reactor 1. After an inside temperature of the tube reactor 1 reached 220° C., dimethylamine was supplied at the temperature to start the reaction. A supplying rate of dimethylamine was controlled according to progress of the reaction, and a reaction time-averaged rate of 67 g/hr. A reaction mixture was analyzed over time by gas chromatography. When an amount of unreacted lauryl alcohol was reduced to 1% (5.5 hours after the start of the reaction), supply of dimethylamine was stopped to finish the reaction. A sample of the reaction mixture at the end of the reaction was collected to determine quantities of ingredients by the area percentage method of gas chromatograph. A reactivity per weight of catalytically active substance, α [/hr/%-catalytically active substance], was determined by the following formula (1). Results are shown in Table 2.

$$\alpha = \frac{\ln C}{0.5 \left( \frac{w\left(\frac{100}{100+p}\right)}{1000} \times 100 \right)} \quad (1)$$

wherein, C represents a concentration of unreacted alcohol 0.5 hours before the reaction end [%]; w represents a weight of the film catalyst [g]; p represents a content of nonvolatile matters of the phenol resin in the film catalyst [parts by weight relative to 100 parts by weight of the powder catalyst]; and ln represents logarithm natural.

Comparative Example 1

A catalyst was similarly reduced as in Example 1, except that a reduction temperature of the catalyst was 200° C. and a reduction time was 90 minutes.

After the reduction of the catalyst, 750 g of lauryl alcohol (Kalcol 20, manufactured by Kao Corporation) was charged in the buffer tank 2. While supplying a hydrogen gas to the tube reactor 1 at a flow rate of 16.5 L/hr based on a standard state volume, a reaction mixture was circulated at 5.9 L/hr between the buffer tank 2 and the tube reactor 1. After an inside temperature of the tube reactor 1 reached 220° C., dimethylamine was supplied at the temperature to start the reaction. A supplying rate of dimethylamine was controlled according to progress of the reaction, and a reaction time-averaged rate of 65 g/hr. A reaction mixture was analyzed over time by gas chromatography. When an amount of unreacted lauryl alcohol was reduced to 1% (6.7 hours after the start of the reaction), supply of dimethylamine was stopped to finish the reaction. A sample of the reaction mixture at the end of the reaction was collected to determine quantities of ingredients by the area percentage method of gas chromatograph. A reactivity per weight of catalytically active substance, α, was similarly determined as in Example 1. Results are shown in Table 2.

TABLE 2

|  |  | Example 1 | Comparative example 1 |
|---|---|---|---|
| Kind of film catalyst | | Catalyst A | Catalyst A |
| Condition of reduction of film catalyst | | | |
| Reduction temperature | [° C.] | 130 | 200 |
| Reduction time | [minutes] | 360 | 90 |
| Evaluation of reaction | | | |
| Reactivity α | [1/hr/%] | 2.3 | 1.9 |
| Reaction time | [hr] | 5.5 | 6.7 |
| Remaining amount of unreacted alcohol | [%] | 1.0 | 1.0 |
| DM*[1] | [%] | 86.5 | 87.7 |
| M2*[2] | [%] | 10.5 | 10.4 |

*[1]N-dodecyl-N, N-dimethylamine
*[2]N, N-didodecy-N-methylamine

Example 2

Using a bubbling tank reactor shown in FIG. 2, N,N-didecyl-N-methylamine was produced from decyl alcohol and monomethylamine by the method described below.

The film catalyst B prepared in Production Example 2 was put in the reaction tank 7. A volume of a part loaded with the film catalyst B was 276 mL. The film catalyst B formed plural flow channels having a cross-sectional area of about 0.1 cm² and leading to the vertical direction of the reaction tank 7. 600 g of decyl alcohol (Kalcol 10, manufactured by Kao Corporation) was charged in the reaction tank 7. While supplying a hydrogen gas to the reaction tank 7 at 9.2 L/hr based on a standard state volume, or a gas space velocity of 33 (1/hr), the catalyst was reduced. 360 minutes after an inside temperature of the reaction tank 7 reached 130° C., reduction of the catalyst was stopped, and the whole mixture in the reaction tank 7 was removed.

After the reduction of the catalyst, 600 g of decyl alcohol (Kalcol 10, manufactured by Kao Corporation) was charged in the reaction tank 7. While supplying a hydrogen gas to the reaction tank 7 at 9.2 L/hr based on a standard state volume, an inside temperature of the reaction tank 7 was increased to 220° C. Then, monomethylamine was supplied at the temperature to start the reaction. A supplying rate of monomethylamine was controlled according to progress of the reaction, and a reaction time-averaged rate of 18 g/hr. A reaction mixture was analyzed over time by gas chromatography. When an amount of unreacted decyl alcohol was reduced to 5% (3.9 hours after the start of the reaction), supply of monomethylamine was stopped to finish the reaction. A sample of the reaction mixture at the end of the reaction was collected to determine quantities of ingredients by the area percentage method of gas chromatograph. A reactivity per weight of catalytically active substance, α, was similarly determined as in Example 1. Results are shown in Table 3.

Example 3

A catalyst was similarly reduced as in Example 2, except that the film catalyst C prepared in Production Example 3 was used instead of the film catalyst B.

After the reduction of the catalyst, 600 g of decyl alcohol (Kalcol 10, manufactured by Kao Corporation) was charged in the reaction tank 7. While supplying a hydrogen gas to the reaction tank 7 at 9.2 L/hr based on a standard state volume, an inside temperature of the reaction tank 7 was increased to 220° C. Then, monomethylamine was supplied at the temperature to start the reaction. A supplying rate of monomethylamine was controlled according to progress of the reaction, and a reaction time-averaged rate of 19 g/hr. A reaction mixture was analyzed over time by gas chromatography. When an amount of unreacted lauryl alcohol was reduced to 5% (3.5 hours after the start of the reaction), supply of monomethylamine was stopped to finish the reaction. A sample of the reaction mixture at the end of the reaction was collected to determine quantities of ingredients by the area percentage method of gas chromatograph. A reactivity per weight of catalytically active substance, α, was similarly determined as in Example 1. Results are shown in Table 3.

TABLE 3

|  |  | Example 2 | Example 3 |
|---|---|---|---|
| Kind of film catalyst |  | Catalyst B | Catalyst C |
| Reduction condition of film catalyst |  |  |  |
| Reduction temperature | [° C.] | 130 | 130 |
| Reduction time | [minutes] | 360 | 360 |
| Evaluation of reaction |  |  |  |
| Reactivity α | [1/hr/%] | 0.2 | 0.3 |
| Reaction time | [hr] | 3.9 | 3.5 |
| Remaining amount of unreacted alcohol | [%] | 5.0 | 5.0 |
| DM*[1] | [%] | 0.34 | 0.38 |
| M2*[2] | [%] | 88.4 | 89.3 |

*[1]N-decyl-N, N-dimethylamine
*[2]N, N-didecyl-N-methylamine

The invention claimed is:

1. A method for producing a tertiary amine, comprising reacting an alcohol with a primary or secondary amine in the presence of a film catalyst comprising a thermosetting resin and an active metal, wherein the film catalyst is reduced at 110 to 140° C.,
wherein an alcohol used in the reduction of the film catalyst is wholly substituted with a new alcohol as a starting alcohol for producing the tertiary amine.

2. The method according to claim 1, wherein the film catalyst is cured at 80 to 170° C.

3. The method according to claim 1 or 2, wherein the thermosetting resin is a phenol resin.

4. The method according to claim 1, wherein the active metal comprises copper.

5. The method according to claim 1, wherein a reduction time is 30 to 600 minutes.

6. The method according to claim 1, wherein the film catalyst is fixed on a surface of a support and has a thickness of 0.01 to 500 μm, excluding the support, after having been cured.

7. The method according to claim 1, wherein the alcohol is a saturated or unsaturated aliphatic alcohol having 8 to 36 carbon atoms, and the primary or secondary amine is an aliphatic primary or secondary amine.

8. The method according to claim 1, wherein the reaction step has a reaction temperature of 150 to 300° C.

* * * * *